United States Patent [19]

Howes et al.

[11] Patent Number: 4,490,330

[45] Date of Patent: Dec. 25, 1984

[54] SULPHUR DIOXIDE-LIBERATING, STERILIZING COMPOSITION AND METHOD OF USING SAME

[75] Inventors: John G. B. Howes, Hertford Heath; Rupert A. Selway, Harlow, both of England

[73] Assignee: Anchor Continental Inc., Columbia, S.C.

[21] Appl. No.: 464,980

[22] Filed: Feb. 8, 1983

[30] Foreign Application Priority Data

Feb. 12, 1982 [GB] United Kingdom ............... 8204134

[51] Int. Cl.³ .................... A61L 13/00; A01N 11/00
[52] U.S. Cl. ...................................... 422/29; 252/105; 252/188.21; 252/188.23; 252/188.24; 252/188.31; 424/162; 424/164; 424/322
[58] Field of Search ............... 252/105, 106, 188.21, 252/188.23, 188.24, 188.31; 8/110, 111; 422/29; 424/162, 164

[56] References Cited

U.S. PATENT DOCUMENTS

| | | | |
|---|---|---|---|
| 3,149,042 | 9/1954 | Habicht et al. | 252/105 |
| 3,207,694 | 9/1965 | Gogek | 252/105 |
| 3,259,457 | 7/1966 | Sauls et al. | 252/188.23 |
| 4,082,683 | 4/1978 | Galesloot | 252/105 |
| 4,128,397 | 12/1978 | Lynch | 422/29 |

FOREIGN PATENT DOCUMENTS 27401 3/1977 Japan.
951290 3/1964 United Kingdom.

*Primary Examiner*—Prince E. Willis
*Attorney, Agent, or Firm*—Jacobs & Jacobs

[57] ABSTRACT

A composition which is capable of releasing sulphur dioxide in the presence of water over an extended period contains a sulphur dioxide-liberating compound and hydroquinone. The composition may also contain thio urea and/or a phosphate buffer. The compositions are used to sterilize soiled articles, such as surgical and sanitary dressings, which have been placed in temporary disposal units prior to permanent disposal.

10 Claims, No Drawings

SULPHUR DIOXIDE-LIBERATING, STERILIZING COMPOSITION AND METHOD OF USING SAME

The invention relates to compositions capable of giving extended release of sulphur dioxide in the presence of moisture and their use for sterilising articles.

Articles which have been soiled by body fluids such as blood, wound exudate, urine and the like are an extremely efficient medium for bacterial growth. Certain of these soiled articles such as soiled sanitary and surgical dressings require permanent disposal, for example, by incineration. Such soiled articles however are often disposed of temporarily in suitable storage containers, for example, a plastic film-lined bin prior to collection for disposal. This storage period can vary considerably depending on factors such as the location of the bin and its frequency of use. For example, a disposal container for sanitary dressings in public conveniences may not be emptied for a period of days or even weeks.

It therefore is highly desirable that such soiled articles be temporarily stored under conditions which would inhibit the growth of bacteria on the articles and consequently prevent any odours associated therewith.

One known method for the temporary disposal of soiled articles is to place them into a liquid disinfectant medium, such as formaldehyde, but this generally involves the need for saturation of the articles with the medium, which can present problems if the disposal unit becomes too full. Moreover, over a period of time, antibacterial or disinfectant liquid becomes weakened, and, in any case, the volume of liquid that must be present in the disposal unit limits the number of articles that can be placed into the unit.

Sulphur dioxide has been known for many years to be a very efficient sterilising agent, both in solution and in vapour form in a moist atmosphere. The main problem associated with the use of sulphur dioxide for such purposes as the temporary disposal of for example soiled dressings is that its sterilising action is transitory. This is because most chemical reactions producing sulphur dioxide are fast reactions with the gaseous sulphur dioxide being evolved fairly quickly and the reaction being exhausted after a fairly short period of time. The sulphur dioxide produced gradually diffuses into the atmosphere and leaves a residual concentration of sulphur dioxide that is insufficient to be effective.

Sulphur dioxide has been found to be an excellent sterilising medium for articles such as, for example, soiled sanitary and surgical dressings, in that it reduces bacterial growth very considerably or even eliminates it. It has the additional advantage that, because of its reducing action, it has an inhibiting effect on oxidation reactions, which frequently produce malodours. Compositions capable of giving extended release of sulphur dioxide are known. These compositions contain a compound that will liberate sulphur dioxide in the presence of water (hereinafter referred to as 'sulphur dioxide-liberating compounds') and a thiosulphate and/or a phosphate which acts as a so-called sulphur dioxide-liberation moderator. It has now been found that by using hydroquinone as a sulphur dioxide-liberation moderator then less moderator is required as compared to thiosulphate but will still generate a high level of sulphur dioxide which is maintained for a sufficiently long period.

The present invention provides a composition capable of giving extended release of sulphur dioxide in the presence of moisture, which comprises a compound that will liberate sulphur dioxide on contact with water and hydroquinone.

From the above it is clear that the skilled worker will appreciate that the present invention provides a composition capable of releasing sulphur dioxide in the presence of water which composition comprises a sulphur dioxide-liberating compound and a moderator which moderates the liberation of sulphur dioxide characterised in that the moderator is hydroquinone.

By using such a composition in a closed, but periodically opened, container such as a disposal unit for sanitary dressings, it is possible to maintain an active concentration of sulphur dioxide within the container for a period of up to several weeks.

Compounds that will liberate sulphur dioxide in the presence of water are well known. Metabisulphites and dithionites, for example, will decompose in the presence of water with the liberation of sulphur dioxide, and these compounds have been found to be particularly suitable for use as sulphur dioxide-liberating compounds in the compositions according to the invention. They are conveniently used in the form of the respective sodium salts ($Na_2S_2O_5$ and $Na_2S_2O_4$ respectively) since these are readily obtainable.

In a composition according to the invention, hydroquinone serves as a sulphur dioxide-liberating moderator, that is to say that it decreases the rate at which the sulphur dioxide is liberated from the sulphur dioxide-liberating compound as compared with the rate at which it would be liberated in the absence of hydroquinone. That is not to say that the presence of hydroquinone results in the liberation of subsequently less sulphur dioxide than would be liberated in the absence of hydroquinone, but that it results in the liberation of substantially the same amount of sulphur dioxide as would be liberated in the absence of hydroquinone, but at a lower rate and thus over an extended period of time. Thus, the composition according to the invention is described as being "capable of giving extended release of sulphur dioxide".

The amount of hydroquinone present in compositions of the invention can vary according to the rate of sulphur dioxide liberation desired.

The amount of hydroquinone in compositions for sterilising soiled articles such as sanitary dressings can be suitably from 2 to 20 parts by weight and preferably from 6 to 12 parts by weight per 100 parts by weight of the sulphur dioxide-liberating compound.

Other materials may be present in the composition in addition to hydroquinone to enhance the moderating effect of hydroquinone and/or extend the release of sulphur dioxide from the composition on contact with water. A preferred compound of this type is thiourea. Accordingly in another aspect the invention provides a composition capable of giving extended release of sulphur dioxide in the presence of moisture, which comprises a compound that will liberate sulphur dioxide on contact with water, hydroquinone and thiourea.

It is clear that in another aspect the present invention provides a composition capable of giving release of sulphur dioxide in the presence of water which composition comprises a sulphur dioxide-liberating compound and a moderator which moderates the liberation of sulphur dioxide characterised in that the moderator is hydroquinone and thiourea.

It has been found that compositions of the invention containing both hydroquinone and thiourea have a reduced rate of sulphur dioxide liberation on contact with water when compared with similar compositions containing hydroquinone alone.

Suitable compositions of the invention for sterilising of soiled articles such as sanitary dressings contain 0.5 to 10 parts by weight and preferably 1 to 6 parts by weight of thiourea per 100 parts by weight of the sulphur dioxide-liberating compound.

The ratio of thiourea to hydroquinone in the composition will vary depending upon the level and rate at which sulphur dioxide is to be liberated. Generally the ratio of thiourea to hydroquinone in the composition is suitably 1:6 to 1:1 and is preferably 1:3 to 2:3.

Compositions of the invention may also contain a buffer. The presence of a buffer in the composition can extend the release of sulphur dioxide from the composition when contacted with water. The mechanism by which buffers extend the release of sulphur dioxide from the compositions is not understood. It is possible that the pH at which the buffer maintains an aqueous solution of the composition can affect the rate of sulphur dioxide liberation and/or the amount of the sulphur dioxide-liberating compound converted to sulphur dioxide.

Suitable buffers include phosphates, orthophosphates and borates. Favoured buffers include water-soluble, dihydrogen orthophosphate salts of which $KH_2PO_4$ is preferred. Compositions for sterilising soiled articles such as sanitary dressings can contain 10 to 50 parts by weight and preferably 20 to 30 parts by weight of a phosphate buffer per 100 parts by weight of the sulphur dioxide-liberating compound.

The relative amounts in the composition of the sulphur dioxide-liberating compound, hydroquinone and other materials which enhance the moderating effect of hydroquinone and/or extend the release of sulphur dioxide from the composition can vary according to the rate of sulphur dioxide liberation desired. It may be desired, for example, for the composition to liberate sulphur dioxide at a substantially constant rate over a period of several days or even weeks; this can be particularly advantageous for use in such situations as disposal units for sanitary dressings in public conveniences as described above. Alternatively, it may be desired to liberate sulphur dioxide at a gradually decreasing rate; this can be useful in situations where it is desired to establish fairly rapidly an active concentration of sulphur dioxide and then to maintain an active concentration over a period of time by the continued liberation of sulphur dioxide at a decreased rate to compensate for leakage of the sulphur dioxide. Furthermore, it may be desired to liberate sulphur dioxide at an initially increasing rate and then at a decreasing rate and this can be useful where it is desired to effect a gradual build-up of the concentration of sulphur dioxide and then to maintain an active concentration. In all cases, however, the sulphur dioxide is liberated over a period of time greater than that over which it would be liberated in the absence of hydroquinone.

Favoured compositions contain 100 parts by weight of sodium metabisulphite, 4 to 8 parts by weight of hydroquinone and 20 to 30 parts by weight of potassium dihydrogen orthophosphate.

Further favoured compositions contain 100 parts by weight of sodium metabisulphite, 4 to 8 parts by weight of hydroquinone and 1 to 4 parts by weight of thiourea.

Preferred compositions contain 100 parts by weight of sodium metabisulphite, 4 to 8 parts by weight of hydroquinone, 1 to 4 parts by weight of thiourea and 20 to 30 parts by weight of potassium dihydrogen orthophosphate.

If desired, small amounts of perfume can be included in the composition in order to mask any sulphur dioxide odour.

Compositions of the invention are preferably in particulate form. Such particulate compositions will dissolve rapidly in water and their use therefore lessens the chances of a soiled sanitary dressing being put into a disposal unit before the sterilising composition has dissolved.

The compositions of the invention will usually be packed in a sealed container to prevent the composition reacting with moisture in the atmosphere. A preferred container consists of a sealed sachet containing a predetermined amount of the composition suitable for sterilising a disposal unit of given size. Advantageously the sachet can be made of a water soluble film. Such sachets containing the compositions can be used to form an aqueous sterilising solution without the need to open the sachet.

Suitable water soluble films include films of polyvinyl alcohol and polyethylene oxide. Such water soluble films are readily available. Preferred water soluble films comprise polyvinyl alcohol with a degree of hydrolysis of 87% to 89% and a molecular weight of 44000 to 72000. A favoured film of this type is known as Hi-Selon C available from British Traders and Shippers Limited.

Water soluble film sachets can be conveniently formed from the film by heat sealing or any other convenient method. The sachets can be packed individually or as groups in sealed moisture vapour impermeable containers. Preferred containers include aluminium foil pouches and polyethylene pouches.

The present invention also provides a method for sterilising an article, especially a soiled sanitary dressing or a soiled surgical dressing which comprises bringing the article into contact with or into the proximity of a composition according to the invention in the presence of moisture.

Preferably the article is brought into contact with or into the proximity of the composition in the form of an aqueous solution.

The term "sterilise" as used herein means to cause a substantial reduction in the number of micro-organisms but it is not intended to imply that complete sterility is imparted to the article in the sense that all microorganisms are completely destroyed.

By bringing the article into the proximity of the composition, it is meant that the article may not be brought into actual contact with the composition, but is brought sufficiently near thereto to be sterilised by sulphur dioxide being liberated from the composition. It follows that the article must be brought into a region in which there is an active concentration on sulphur dioxide. The article may, for example, be put into the upper region of a disposal unit for sanitary dressings or other vessel containing a small amount of a composition according to the invention in the form of an aqueous solution.

In order for the sulphur dioxide to impart sterility to an article the concentration of sulphur dioxide in the region of the article should generally be at least 20 ppm (parts by weight of sulphur dioxide per million parts by volume of air) although the concentration required in any particular situation will depend on the ambient temperature. The term "active concentration" simply means a concentration sufficient to impart sterility to the article. Advantageously, the concentration of sulphur dioxide in the region of the article should be within the range of from 75 to 300 ppm.

The method of the invention is advantageously carried out in a closed container as this hinders or prevents the diffusion of the sulphur dioxide into the atmosphere and thus more readily enables an active concentration of sulphur dioxide to be maintained. It also has the advantage that the operator or user is not subjected to the unpleasantness of the presence of sulphur dioxide or at least that such unpleasantness is minimised.

The compositions and method of the invention are particularly suitable for use in closed containers of the so-called "trap-top" type, that is to say containers having a pivoted top which when opened presents a shelf on which the article to be placed in the container can be placed while keeping the container sealed and which allows the article to drop into the container when the lid is closed. Such containers remain sealed at all times and thus leakage of sulphur dioxide is reduced to a minimum. Containers of this type are particularly suitable for use as disposal units for soiled sanitary and surgical dressings. They can be charged with a small quantity of a composition according to the invention in the form of an aqueous solution and can then be put into use for up to several weeks, for example 3 to 4 weeks, during which time soiled dressings may be placed in the container as required. When full, or after a set interval of time, the container can be replaced by a freshly-charged container and then be taken to a disposal site where it can be emptied and the contents destroyed for example by incineration.

It is possible, using the compositions according to the invention, to maintain a sulphur dioxide concentration of from 75 to 300 ppm within such containers for a period of 3 to 4 weeks and in some cases for 6 or more weeks. A concentration of this magnitude is generally sufficient to maintain all soiled dressings or other articles within the container in a sterile state until their permanent disposal. This has been found to be the optimum sulphur dioxide concentration range, although concentrations outside this range may be used in certain cases. The concentration should not, however, generally be less than 20 ppm, since there is then a danger of it being ineffective, or more than 700 ppm, since there is then a danger of unpleasantness to persons in the vicinity of the container.

Sterilising solutions for the disposal units can be prepared by dissolving a composition of the invention in water and pouring the solution into the unit. Alternatively the compositions, preferably in water soluble film sachets, can be added to water already in the disposal unit.

The invention is illustrated by the following Examples.

The term "ppm" used throughout the Examples to indicate the sulphur dioxide ($SO_2$) concentration means parts by weight of sulphur dioxide per million parts by volume of air.

EXAMPLES 1 TO 4

Three compositions of the invention (Examples 2, 3 and 4) and a comparison composition containing sodium metabisulphite only were prepared for $SO_2$ release tests:

|  | Example | | | |
| --- | --- | --- | --- | --- |
|  | 1 | 2 | 3 | 4 |
| Sodium metabisulphite | 9.50 g | 9.50 g | 9.50 g | 9.50 g |
| Hydroquinone | — | 0.50 g | 0.50 g | 0.50 g |
| Thiourea | — | — | — | 0.82 g |
| Potassium dihydrogen orthophosphate | — | — | 2.72 g | 2.72 g |

$SO_2$ Release Test

Each composition of the Examples was dissolved in 200 ml of water in a glass beaker (250 ml) and stored at 20° C. The available $SO_2$ remaining in the solutions was determined over a period of 1 to 55 days by means of a standard analytical procedure by reacting an aliquot taken from each solution with excess acidified iodine solution and titrating the unreacted iodine with a solution of sodium thiosulphate. The following results were obtained:

|  | Period (days) | | | | | | | | | | |
| --- | --- | --- | --- | --- | --- | --- | --- | --- | --- | --- | --- |
|  | % available $SO_2$ (ppm) in solution | | | | | | | | | | |
| Example | 0 | 1 | 2 | 5 | 6 | 10 | 20 | 27 | 34 | 48 | 55 |
| 1 | 100 | 71.7 | 39.8 | 1.7 | 0 | — | — | — | — | — | — |
| 2 | 100 | — | — | — | 86.3 | 81.1 | 72.1 | 63.2 | 56.8 | 42.1 | 34.2 |
| 3 | 100 | — | — | — | 84.6 | 81.7 | 70.0 | 61.7 | 54.3 | 39.9 | 31.4 |
| 4 | 100 | — | — | — | 84.0 | 79.0 | 74.0 | 68.0 | — | — | — |

The results show that the compositions of the invention (Examples 2, 3 and 4) in aqueous solution have available $SO_2$ over a long period of time (55 days) indicating that they give an extended release of $SO_2$ in contact with water when compared with that of the comparison composition of Example 1 (no available $SO_2$ after 6 days) containing sodium metabisulphite only.

EXAMPLE 5

A composition containing sodium metabisulphite (50 g), potassium dihydrogen orthophosphate (13.6 g) and hydroquinone (6 g) was dissolved in water (1 liter) and the solution placed at the bottom of a "trap-top" disposal bin (45 liter size). The bin was stored at ambient room temperature (18° C. to 20° C.). To simulate normal use the trap top was opened and shut three times each day. The $SO_2$ level (ppm) inside the bin was measured over a period of 21 days by means of Dräger (registered trade mark) tubes. The results were as follows:

|  | Period (days) | | | | | | | | |
| --- | --- | --- | --- | --- | --- | --- | --- | --- | --- |
|  | 0.13 | 1 | 2 | 4 | 7 | 11 | 14 | 18 | 21 |
| $SO_2$ level (ppm) | 180 | 200 | 220 | 300 | 400 | 525 | 500 | 450 | 375 |

The results confirmed that a composition containing hydroquinone gives extended release of SO₂.

EXAMPLES 6 TO 8

Compositions containing both hydroquinone and thiourea in various proportions were prepared.

|  | Example 6 | Example 7 | Example 8 |
| --- | --- | --- | --- |
| Sodium metabisulphite | 50 g | 50 g | 50 g |
| Potassium dihydrogen orthophosphate | 13.6 g | 13.6 g | 13.6 g |
| Hydroquinone | 3 g | 3 g | 3 g |
| Thiourea | 4 g | 2 g | 1 g |

The composition of each Example was dissolved in water (1 liter) and the solutions placed at the bottom of "trap top" disposal bins (45 liter size) and the bins stored at ambient room temperature (18° C. to 20° C.). A sanitary towel (Dr. Whites No. 1 looped towel available from Southalls Limited) was posted into each bin at intervals throughout the day (3 per day) to simulate normal use. The SO₂ levels (ppm) inside the bins were measured over a period of 45 days by means of Dräger tubes. The following results were obtained:

| Example No. | Period (days) | | | | | | |
| --- | --- | --- | --- | --- | --- | --- | --- |
|  | 0.27 | 3 | 10 | 17 | 31 | 38 | 45 |
|  | SO₂ level (ppm) | | | | | | |
| 6 | 110 | 145 | 375 | 500 | 350 | 300 | 320 |
| 7 | 115 | 145 | 280 | 375 | 260 | 220 | 280 |
| 8 | 110 | 180 | 300 | 350 | 260 | 220 | 250 |

The results show that under simulated conditions of use all the compositions gave extended release of SO₂ in contact with water.

EXAMPLE 9

A composition containing sodium metabisulphite (50 g), potassium dihydrogen orthophosphate (13.6 g) and hydroquinone (6 g) was packed into a water soluble film sachet. The sachet was formed from 10 cm × 7½ cm sheet of 10 micron thick polyvinyl alcohol film (High Selon C film) by folding the sheet in two and heat sealing the folded sheet along its three open sides.

EXAMPLE 10

A composition containing sodium metabisulphite (50 g), potassium dihydrogen orthophosphate (13.6 g), hydroquinone (6 g) and thiourea (2 g) was packed into a water soluble film sachet in the same manner as that of Example 9. The composition of Examples 9 and 10 were placed into separate "trap top" bins (size 45 liters) containing water (1 liter) and allowed to dissolve. The bins were stored at ambient room temperature (18° C. to 20° C.). A sanitary towel (Dr. Whites No. 1 looped towel available from Southalls Limited) was posted into each bin at intervals throughout the days (3 per day) to simulate normal use.

The SO₂ levels (ppm) inside the bins were measured over a period of 55 days by means of Dräger tubes. The following results were obtained:

| Example | Period (days) | | | | | | | | | | |
| --- | --- | --- | --- | --- | --- | --- | --- | --- | --- | --- | --- |
|  | 0.13 | 1 | 2 | 7 | 14 | 21 | 28 | 35 | 42 | 48 | 55 |
|  | SO₂ Level (ppm) | | | | | | | | | | |
| 9 | 35 | 85 | 180 | 650 | 700 | 725 | 480 | 425 | 380 | — | — |
| 10 | 60 | 55 | 90 | 240 | 425 | 320 | 320 | 275 | 250 | 220 | 300 |

EXAMPLE 11

A composition containing sodium metabisulphite (25.74 g), potassium dihydrogen phosphate (7.20 g), hydroquinone (1.54 g) and thiourea (0.52 g) was sealed inside a polyethylene sachet. For use, the sachet was opened and the contents dissolved in water (500 ml) in a trap top bin (size 40 liters). The sulphur dioxide-level in the bin was maintained in the preferred range of 75 to 300 ppm for a period of 55 days.

Sterility Tests

A sanitary towel (Dr. Whites No. 1 ) and a similar towel wrapped in a paper bag were each inoculated with $10^5$ organisms of Escherichia coli as suspension in 5 ml quarter strength Ringers solution. The two towels were suspended by strings from the door of the bin containing the composition of Example 9 on 25th day of bin test. The towels were taken out of the bin after 24 hours and an attempt was made to recover the test organisms by immersing the towels in a quarter strength Ringers solution containing Tween 80 (0.1%) and squeezing out the fluid by standard bag technique. Aliquots (9 ml) of the wash fluid were mixed with double strength Tryptone Soya Agar (9 mls) at 80° C. The agar mixture was incubated at 37° C. for 24 hours and plate counts carried out for viable growth. No growth of *E. coli* was found.

In a second test 1 ml aliquots of the wash fluid were mixed with 18 mls of Tryptone Soya Broth and the culture placed onto McConkey agar. The culture was then incubated for 24 hours at 37° C. No viable *E coli* was recorded.

During the 24 hour period of test the level of SO₂ in the bin dropped to 250 ppm.

We claim:

1. A composition capable of releasing sulphur dioxide in the presence of water, which comprises 2 to 20 parts by weight of hydroquinone and 0.5 to 10 parts by weight of thiourea per 100 parts by weight of a sulphur dioxide-liberating compound which is a metabisulphite said hydroquinone and said thiourea being operable to moderate the liberation of sulphur dioxide from said metabisulphite.

2. A composition according to claim 1, which comprises 1 to 6 parts by weight of hydroquinone per part by weight of thiourea.

3. A composition according to claim 2, which also comprises 10 to 50 parts by weight of a phosphate buffer per 100 parts by weight of sulphur dioxide-liberating compound.

4. A composition according to claim 1, which comprises 100 parts by weight of sodium metabisulphite, 4 to 8 parts by weight of hydroquinone and 1 to 4 parts by weight of thiourea.

5. A composition according to claim 4, which also comprises 20 to 30 parts by weight of potassium dihydrogen orthophosphate per 100 parts by weight of sodium metabisulphite.

6. A method of sterilising an article which comprises bringing the article into contact with or into the proximity of an aqueous solution of a composition as claimed in claim 1 whereby the concentration of sulphur dioxide on the region of the article is at least 20 ppm.

7. A method of sterilising an article which comprises bringing the article into contact with or into the proximity of an aqueous solution of a composition as claimed in claim 2 whereby the concentration of sulphur dioxide in the region of the article is at least 20 ppm.

8. A method of sterilising an article which comprises bringing the article into contact with or into the proximity of an aqueous solution of a composition as claimed in claim 3 whereby the concentration of sulphur dioxide on the region of the article is at least 20 ppm.

9. A method of sterilising an article which comprises bringing the article into contact with or into the proximity of an aqueous solution of a composition as claimed in claim 4 whereby the concentration of sulphur dioxide on the region of the article is at least 20 ppm.

10. A method of sterilizing an article which comprises bringing the article into contact with or into the proximity of an aqueous solution of a composition as claimed in claim 5 whereby the concentration of sulphur dioxide in the region of the article is at least 20 ppm.

* * * * *